US010799638B2

(12) United States Patent
Vivien et al.

(10) Patent No.: US 10,799,638 B2
(45) Date of Patent: Oct. 13, 2020

(54) NEEDLELESS INJECTION DEVICE WITH AN ANGULARLY-POSITIONABLE CLOSURE STOPPER

(71) Applicant: CROSSJECT, Dijon (FR)

(72) Inventors: Gilles Vivien, Malakof (FR); Xavier Vigot, Veronnes (FR)

(73) Assignee: CROSSJECT, Dijon (FR)

(*) Notice: Subject to any disclaimer, the term of this patent is extended or adjusted under 35 U.S.C. 154(b) by 219 days.

(21) Appl. No.: 15/849,874

(22) Filed: Dec. 21, 2017

(65) Prior Publication Data

US 2018/0110930 A1    Apr. 26, 2018

Related U.S. Application Data

(63) Continuation of application No. PCT/FR2016/051659, filed on Jun. 30, 2016.

(30) Foreign Application Priority Data

Jun. 30, 2015 (FR) .................................... 15 56157

(51) Int. Cl.
*A61M 5/30* (2006.01)
*A61M 5/20* (2006.01)

(52) U.S. Cl.
CPC ........ *A61M 5/3007* (2013.01); *A61M 5/2046* (2013.01); *A61M 5/30* (2013.01); *A61M 2205/0216* (2013.01)

(58) Field of Classification Search
CPC .............. A61M 5/3007; A61M 5/2046; A61M 2205/0216
USPC .......................................................... 604/70
See application file for complete search history.

(56) References Cited

U.S. PATENT DOCUMENTS

| 2004/0015125 A1* | 1/2004 | Alexandre | ............... A61M 5/30 604/69 |
| 2008/0319383 A1* | 12/2008 | Byland | ............... A61M 5/1782 604/67 |
| 2013/0317431 A1* | 11/2013 | Kramer | ................... A61M 5/30 604/131 |

FOREIGN PATENT DOCUMENTS

| FR | 2815544 | 4/2002 |
| FR | 2978021 | 1/2013 |
| GB | 2046228 | 11/1980 |

OTHER PUBLICATIONS

International Search Report for International Application PCT/FR2016/051659, dated Oct. 25, 2016.

* cited by examiner

*Primary Examiner* — Brandy S Lee
*Assistant Examiner* — Nidah M Hussain
(74) *Attorney, Agent, or Firm* — Burris Law, PLLC

(57) ABSTRACT

The present disclosure is directed towards a needleless injection device that includes a body, a gas generator, an injection system that extends axially along an injection axis and includes at least one plunger, an active ingredient reservoir, an injection nozzle that delimits at least one injection channel, a cover that houses the body of the device, a removable cap that protects a lower downstream end of the injection nozzle, a stopper that houses the cap, and a blocking element. The stopper is pivotally mounted about the injection axis between a closed position in which the stopper is locked on the injection device and an open position in which the stopper is unlocked from the injection device. The blocking element is radially interposed between the cap and the stopper, and is configured to block, by friction, the relative pivoting of the cap and of the stopper, about the injection axis.

12 Claims, 3 Drawing Sheets

NEEDLELESS INJECTION DEVICE WITH AN ANGULARLY-POSITIONABLE CLOSURE STOPPER

CROSS-REFERENCE TO RELATED APPLICATIONS

This application is a continuation of International Application No. PCT/FR2016/051659, filed on Jun. 30, 2016, which claims the benefit of FR 15/56157 filed on Jun. 30, 2015. The disclosures of the above applications are incorporated herein by reference.

FIELD

The present disclosure relates to disposable pre-filled needleless injection devices, operating with an energy source.

BACKGROUND

The statements in this section merely provide background information related to the present disclosure and may not constitute prior art.

The active ingredient is formed of a liquid more or less viscous liquid, a mixture of liquid, or a gel. The active ingredient may also be a solid dissolved in a solvent suitable for the injection or it may be formed by a pulverulent solid suspended at a certain concentration in a suitable liquid. The grain size distribution of the active ingredient must then be compatible with the diameter of the ducts in order to avoid obstructing them.

Generally, an injection device includes, for example as in the patent application FR-A-2815544 (equivalent to WO 02/34317), a body comprising successively a gas generator, an expansion chamber, a reservoir containing the liquid active ingredient and an injection system.

The reservoir is formed by a glass tube which is inserted into the body of the device and which is obstructed by an upstream plunger stopper and a downstream plunger stopper between which the liquid active ingredient is contained.

The downstream free end of the reservoir cooperates with an injection nozzle which delimits at least one injection channel extending axially along an injection axis.

The gas generator is designed to generate a pressurized gas which drives in displacement the plunger stoppers in order to inject the active ingredient through the patient's skin via the injection nozzle.

In addition, the injection device includes a hollow cover which envelops the body and which delimits a lower opening adapted for the passage of the injection nozzle.

The free end of the injection nozzle which protrudes out of the body and of the cover is protected by a removable cap and a stopper which houses the cap.

Generally, to this end, the stopper includes a tubular portion which delimits a housing adapted to house the cap and the protruding lower downstream portion of the nozzle.

The cap is, for example, removably fastened on the nozzle by a bayonet-type locking means.

The unlocking of the cap, which is pivotally secured to the stopper, is performed by pivoting the stopper relative to the cover, about the injection axis, between a closed position in which the stopper and the cover are aligned by having no asperities, and an open position in which the set formed by the stopper and the cap can be removed.

To this end, the cap includes an annular ring which is mounted on its periphery and which delimits a notched peripheral wall whose notches cooperate with teeth of the stopper.

Such a design by cooperation of notches and teeth limits the number of angular positions, about the pivot axis, between the stopper and the set formed by the ring and the cap.

Consequently, when the stopper occupies its closed position, an angular shift may be observed between the stopper and the cover, this shift generating a misalignment of the stopper and of the cover assimilated to a visual defect of the injection device.

In addition, the notched ring being of the rack-type, it enables only one direction of opening of the stopper, for example counterclockwise, which makes the injection device poorly adapted to part of the users.

SUMMARY

The present disclosure aims at overcoming these and other drawbacks and relates to a needleless injection device. In one form, the present disclosure includes a body, a gas generator, and an injection system. The injection system extends axially along an injection axis and comprises at least, from upstream to downstream along the injection direction, a plunger, an active ingredient reservoir, an injection nozzle which delimits at least one injection channel, a cover which houses the body of the device, a removable cap adapted to protect a downstream lower end of the injection nozzle, and a stopper which houses the cap. The stopper is pivotally mounted about the injection axis between a closed position in which the stopper is locked on the injection device and an open position in which the stopper is unlocked from the injection device. The device includes a blocking element which is radially interposed between the cap and the stopper. The blocking element is designed to block, by friction, the relative pivoting of the cap and of the stopper, about the injection axis, during the pivotal driving of the stopper.

In another form, the blocking element offers positioning the cap relative to the stopper in an accurate manner and also offers consequently an accurate angular positioning of the stopper relative to the cover, so that the stopper, in its closed position, is aligned with the cover of the device.

According to one form, the blocking element is a ring which is fastened on a cylindrical peripheral wall of the cap about the injection axis.

In another form, the blocking element is made of an elastically-deformable material.

In yet another form, the blocking element is made of an elastomer.

In one form, the blocking element is made by overmolding on the cap.

According to another form, the stopper includes a tubular portion which delimits a housing adapted to house the cap and the downstream end of the nozzle. The tubular portion is closed at a downstream end by a removable bottom disc, said disc including a plurality of tightening tabs which extend axially from an upper face of the disc and which are each designed to bear radially on the blocking element to pinch and block pivotally the blocking element. In this form, the feature allows an accurate mounting of the cap on the stopper, according to an infinite number of angular positions.

In one form, in order to promote the pinching of the cap, each tightening tab is elastically deformable at least radially toward the center of the cap.

In another form, each tightening tab has an axial rib, forming a tooth, which is adapted to penetrate in a radial manner into the blocking element in order to block pivotally said blocking element relative to the stopper.

In addition, in one form, each tightening tab bears radially against an inner wall of the stopper to constrain said tabs radially toward the blocking element.

In another form, in order to inhibit the intrusion of impurities into the injection channels, the cap has an annular collar which extends about the injection axis and which is adapted to cooperate with the downstream end of the nozzle.

In one form, the injection device includes a first bayonet-type locking means adapted to lock the stopper on the body of the device, during the driving of the stopper between its open position and its closed position.

In one form, the injection device includes a second bayonet-type locking means adapted to lock the cap on the nozzle during the driving of the stopper between its open position and its closed position.

According to another form, the active ingredient contained in the reservoir is selected from the group comprising the following active ingredients: Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medroxyprogesterone acetate, Medroparin calcium, Methylprednisolone acetate, Heparin calcium, Terbutaline.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
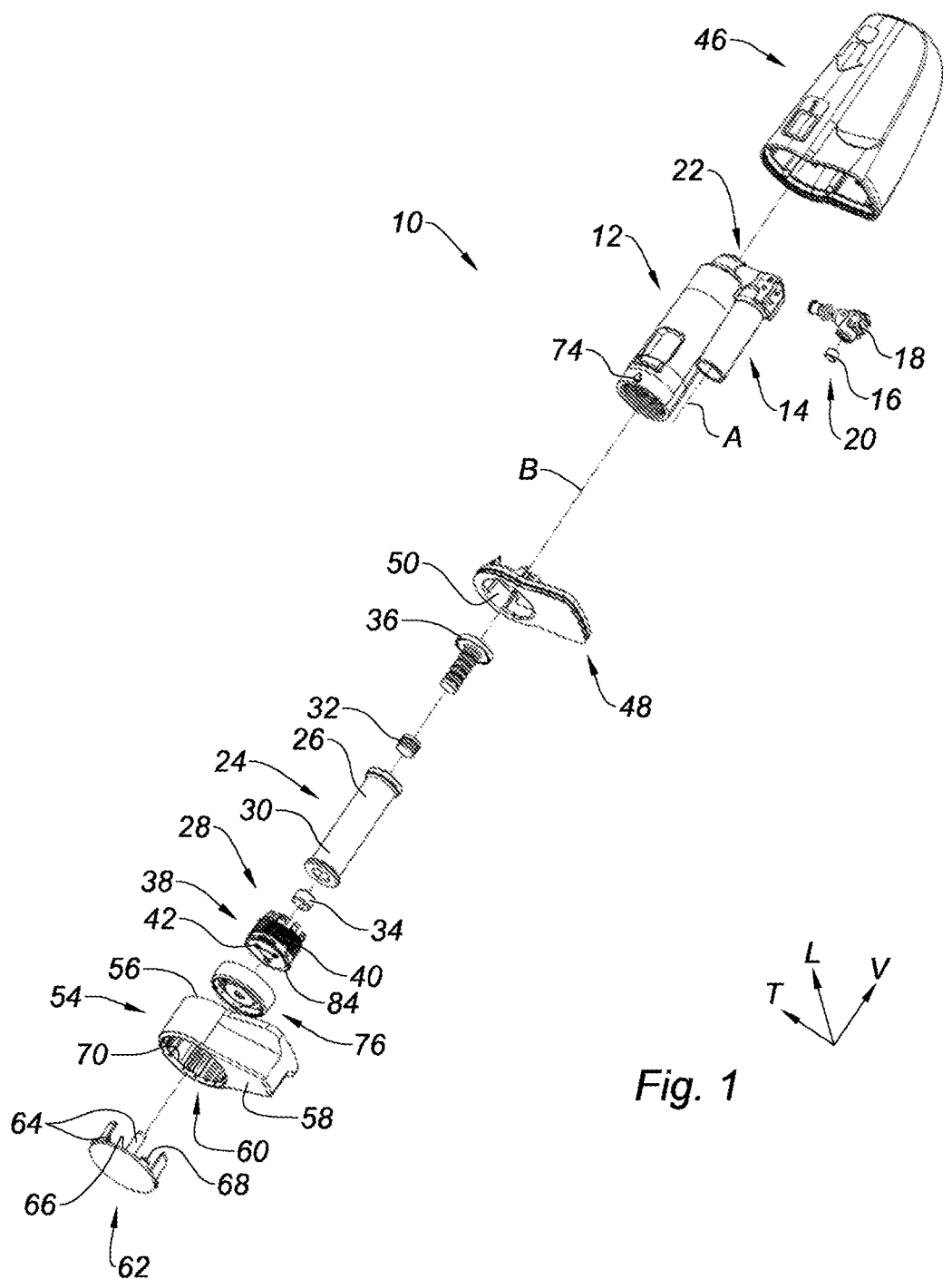
FIG. 1 is an axially exploded perspective view, which illustrates a needleless injection device including a cap and an angularly-positionable closure stopper, according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the description and claims, in order to clarify the description and claims, the longitudinal, vertical and transverse terminology will be adopted without limitation with reference to the trihedron L, V, T indicated in the figures.

It should be noted that in the present patent application, the terms "upstream" and "downstream" should be understood with reference to the circulation of the active ingredient inside the injection device, along an injection direction.

In addition, in the present application, the terms "top", "bottom", "upper", "lower", "horizontal", "vertical", and their derivatives refer to the position or orientation of an element or a component, this position or orientation being considered with reference to the orientation of the device in FIGS. 1 to 6, without reference to the earth's gravity.

FIG. 1 shows a needleless injection device 10, or needleless syringe, which includes a U-shaped body 12 comprising successively a percussion device 14, a primer 16, a pyrotechnic charge 18, these three elements constituting a gas generator 20, an expansion chamber 22, a reservoir 24 containing the liquid active ingredient 26 and an injection system 28.

The gas generator 20 includes a first linear subassembly of the body 12 which extends axially along a first vertical axis A, and the reservoir 24 containing the active ingredient 26 and the injection system 28 form a second linear subassembly of the body 12 which extends axially along a second vertical injection axis B.

These two subassemblies are linked to one another by the expansion chamber 22 which has an axis perpendicular to the axes A, B of the subassemblies.

The reservoir 24 is formed by a glass tube 30 obstructed by an upstream plunger stopper 32 and a downstream plunger stopper 34 between which the liquid active ingredient 26 is contained, the plunger stoppers being made of an elastically-deformable elastomer-based material.

The reservoir 24 is inserted into the body 12 and is blocked vertically at its upstream portion by a cylindrical part 36 provided with a central opening allowing to set the upstream plunger stopper 32 into communication with the expansion chamber 22 and at its downstream portion by an injection nozzle 38.

Figure 2:
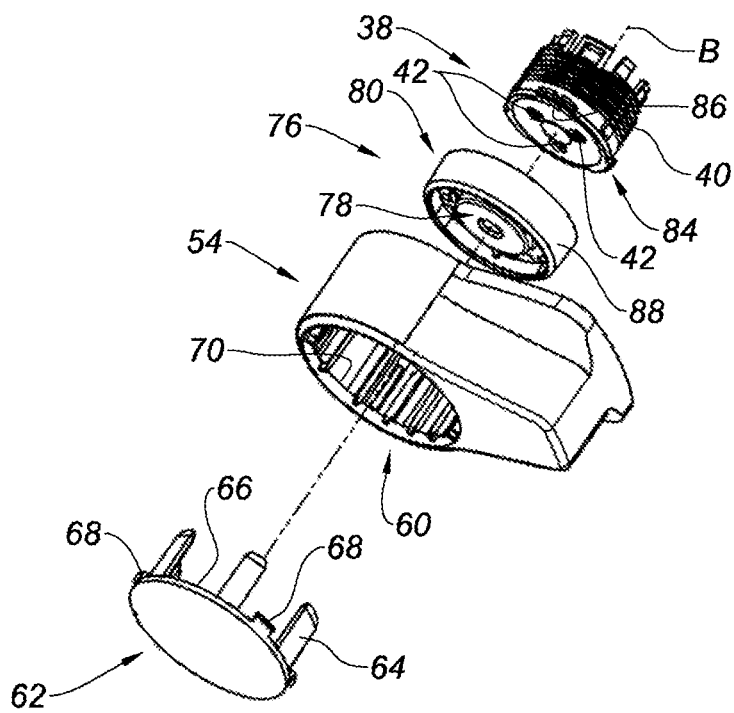
FIG. 2 is a detail perspective view of FIG. 1, which illustrates the nozzle, the cap and the stopper of the device of FIG. 1.
Figure 4:
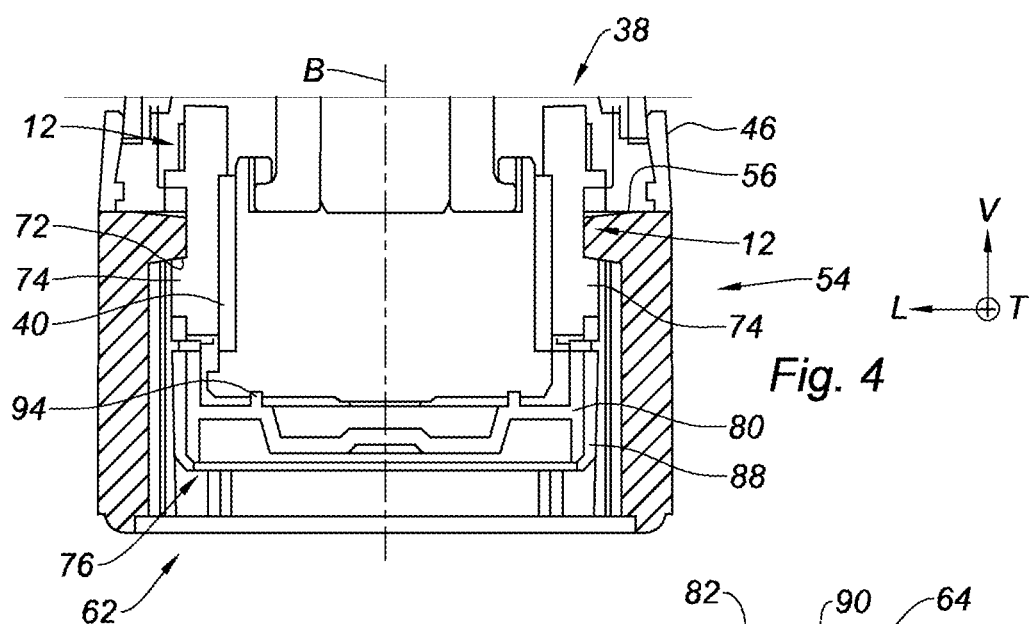
FIG. 4 is a detail axial longitudinal sectional view, which illustrates the cap of FIG. 1 arranged on the nozzle and the stopper in the closed position.

The nozzle 38, shown in more detail in FIGS. 2 and 4, has a cylindrical shape along the injection axis B which is delimited by a cylindrical peripheral face 40 provided with a thread. The thread being intended to cooperate with a complementary tapping formed on the inner wall of the downstream end of the body 12.

In addition, the nozzle 38 delimits three axial injection channels 42 parallel to the injection axis B, illustrated in FIG. 2.

Figure 3:
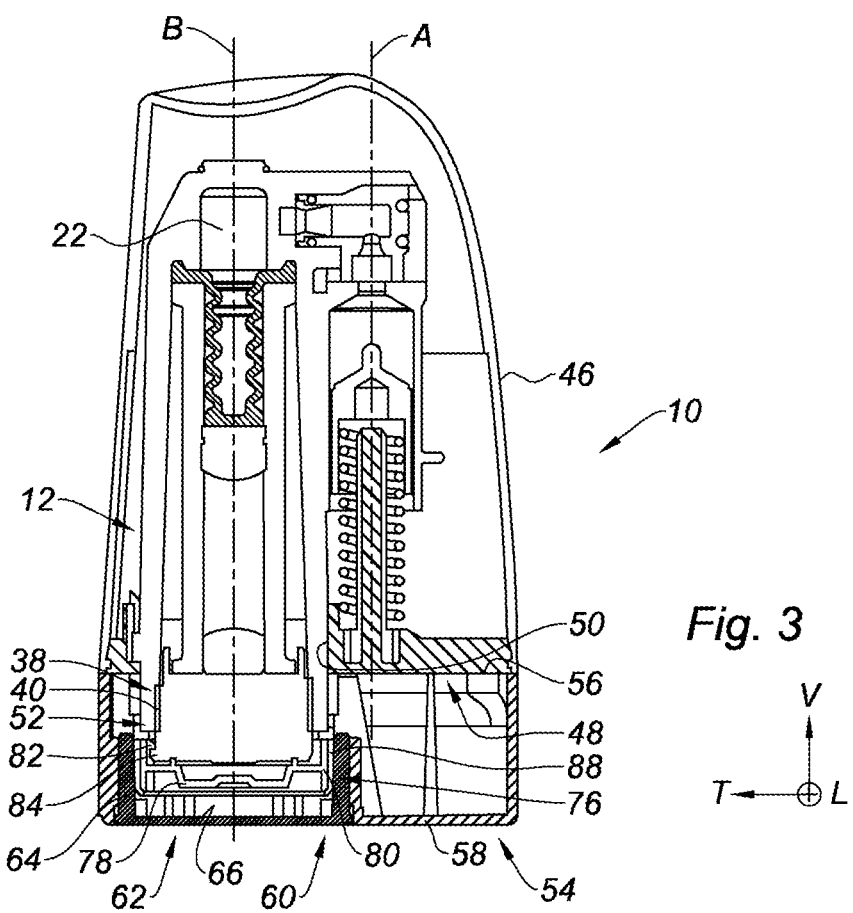
FIG. 3 is an axial cross-sectional view, which illustrates the cap of FIG. 1 arranged on the nozzle and the stopper in the closed position.

According to FIG. 3, the body 12 is enveloped by a hollow cover 46 which delimits a lower opening closed by a horizontal base 48 forming a cover bottom.

The base 48 delimits a circular passage 50 about the injection axis B which is adapted for the passage of the injection nozzle 38 and of the downstream end of the body 12, so that the nozzle 38 includes a lower section 52 protruding vertically downwards out of the cover 46.

Also, the injection device 10 is equipped with a stopper 54 which is delimited vertically by an open upper face 56 bearing on the base 48 of the cover 46, and a generally planar closed lower face 58.

The stopper 54 delimits a generally tubular housing which extends axially along the injection axis B and which opens into the lower face 58 of the stopper 54 by forming a circular passage 60 closed by a removable bottom disc 62.

The bottom disc 62 includes six tightening tabs 64 which extend axially parallel to the injection axis B, from an upper face 66 of the disc 62.

In addition, in order to allow fastening the disc 62 on the stopper 54, the disc 62 includes four elastically-deformable teeth 68 each adapted to cooperate with an inner annular groove 70 formed by the stopper 54.

According to another aspect, the stopper 54 is pivotally mounted about the injection axis B between a closed position in which the stopper 54 is positioned in the extension of the cover 46, so that the stopper 54 and the cover 46 form a homogenous shell without asperities, and an open position in which the stopper 54 is angularly pivoted by about 60 degrees about the injection axis B.

In its closed position, the stopper 54 is locked on the rest of the injection device 10. Conversely, in its open position, the stopper 54 is capable of being removed from the rest of the device 10 in order to enable access to the injection nozzle 38 and to perform an injection.

For this purpose, the injection device 10 includes a first bayonet-type locking means adapted to lock the stopper 54 on the body 12 of the device 10, during the driving of the stopper 54 between its open position and its closed position.

To this end, as shown in FIG. 4, the upper face 56 of the stopper 54 delimits a groove 72 which is designed to cooperate with two lugs 74 (one of which is represented in FIG. 1) which protrude radially from a lower end of the body 12.

In accordance with the present disclosure, the injection device 10 includes a removable cap 76 adapted to obstruct the lower downstream end of the injection nozzle 38.

As shown in FIGS. 2 and 3, the cap 76 is in the form of a cup, which has a radial bottom wall 78 and a cylindrical peripheral crown 80 extending about the injection axis B.

The cap 76 is removably locked on the free end of the injection nozzle 38 by a second bayonet-type locking means.

Figure 5:
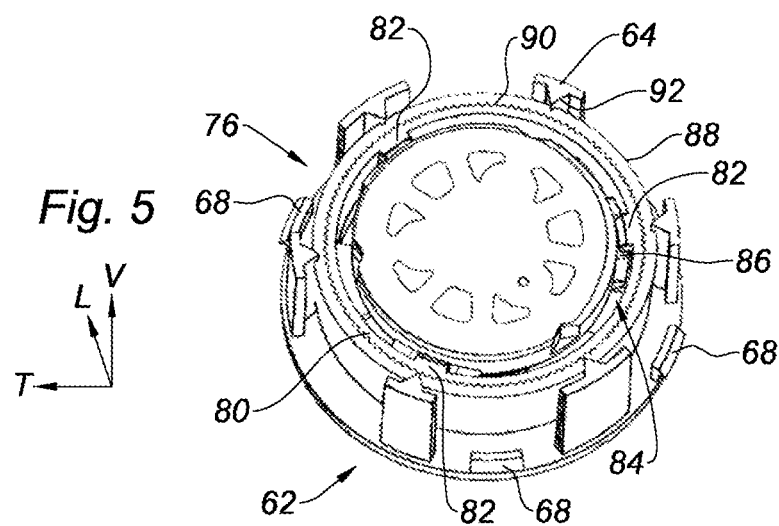
FIG. 5 is a detail perspective radial sectional view, which illustrates the cap and its peripheral ring cooperating with the tabs of the disc of the stopper.
Figure 6:
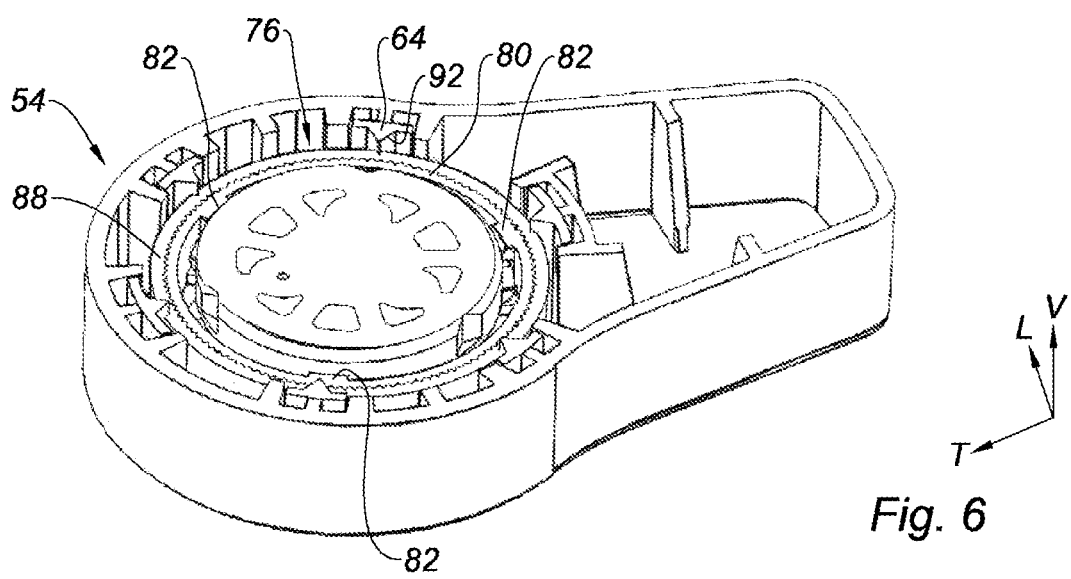
FIG. 6 is a detail perspective radial sectional view, which illustrates the cap and its peripheral ring cooperating with the tabs of the disc of the stopper.

To this end, referring to FIG. 5, the cap 76 includes three lugs 82 which protrude radially toward the center of the cap 76, from an inner wall of the crown 80 of the cap 76, and which are angularly distributed in an even manner at 120 degrees about the injection axis B.

Complementarily, the downstream free end of the nozzle 38 forms a locking collar 84 which extends radially at the periphery of the nozzle 38 and which has three indentations 86 adapted to enable the axial passage of the lugs 82 of the cap 76 beyond the collar 84.

According to another aspect of the present disclosure, the injection device 10 includes a generally cylindrical ring 88, forming a blocking element, which extends about the injection axis B and which is fastened on the outer face of the peripheral crown 80 of the cap 76.

Referring to FIG. 5, the outer face of the peripheral crown 80 of the cap 76 forms axial striations 90 which rotatably block the ring 88 on the cap 76.

Furthermore, the ring 88 is arranged to be radially interposed between the peripheral crown 80 of the cap 76 and the tabs 64 of the disc 62 of the stopper 54.

Also, the ring 88 is designed to block by friction the relative pivoting of the cap 76 and of the stopper 54, about the injection axis B, via the tabs 64 of the bottom disc 62 of the stopper 54.

By friction, is meant a frictional interaction which opposes the relative movement between the cap 76 and the set formed by the stopper 54 and the disc 62, in contrast with a notch-type or rack-type mechanical coupling.

Such a design allows positioning angularly the cap 76 relative to the stopper 54, about the injection axis B, according to an infinite number of angular positions.

In order to enable the pivotal blocking by friction, the blocking ring 88 is made of an elastically-deformable material.

Preferably, the blocking ring 88 is made of an elastomer, and more particularly of a thermoplastic elastomer.

Advantageously, each tightening tab 64 belonging to the disc 62 is elastically deformable radially toward the injection axis B.

Similarly, each tightening tab 64 has an axial rib 92 protruding radially, forming a tooth, which is adapted to penetrate in a substantially radial manner into the blocking ring 88 to pinch and block pivotally the ring 88 relative to the stopper 54, about the injection axis B.

In addition, each tightening tab 64 bears radially against an inner wall of the stopper 54 in order to inhibit the tabs 64 from spacing apart radially toward the outside of the stopper 54 and to constrain the tabs 64 by bearing radially on the ring 88.

According to one form, the blocking ring 88 is made by overmolding on the cap 76 which is made by means of a more rigid thermoplastic-type material.

According to another aspect, the cap 76 has a generally annular collar 94, shown in FIG. 4, which extends about the injection axis B and which bears axially against an elastomer-made gasket (not represented) of the nozzle 38, to protect the downstream free end of the nozzle 38 and in particular the injection channels 42.

An operation example and a mounting example of the injection device 10 according to the present disclosure are described hereinbelow.

The cap 76 is mounted on the bottom disc 62 of the stopper, in a determined angular position, about the injection axis B, the set formed thereby is inserted axially from bottom to top through the circular passage 60 delimited by the stopper 54, so that the disc 62 and the cap 76 are secured to the stopper 54.

Then, the stopper 54 equipped with the cap 76 is mounted on the set formed by the body 12, the cover 46 and the nozzle 38.

To this end, the stopper 54 is presented in an angularly pivoted position corresponding to its open position before being driven axially upwards so as to engage the first bayonet-type locking means of the stopper 54 on the body 12, and the second bayonet-type locking means of the cap 76 on the free end of the injection nozzle 38.

Once in its open position, the stopper 54 is pivoted about the injection axis B to its closed position in order to lock simultaneously the stopper 54 on the body 12 and to lock the cap 76 on the nozzle 38.

The removal and the unlocking of the stopper 54 are carried out, conversely, by driving the stopper 54 from its closed position to its open position.

Advantageously, the device 10 according to the present disclosure allows pivotally driving the stopper between its open position and its closed position both in a pivot direction as well as in another direction, about the injection axis B.

In addition, the blocking ring 88 mounted on the cap 76 offers an accurate angular positioning of the cap 76 with respect to the stopper 54 and also offers, consequently, an accurate angular positioning of the stopper 54 with respect to the cover 46, so that the stopper 54, in its closed position, is perfectly aligned with the cover 46 of the device 10.

As regards the operation of the injection device 10 succinctly described in the following, it is similar to the operation of the device described in the document FR-A-2815544.

The user unlocks the injection device 10 by taking off the stopper 54 by a rotation in either direction. He applies the free end of the nozzle 38 against the skin of the patient to be treated and, by a thumb pressure, he pushes the cover 46 which slides along the body 12 until triggering the gas generator 20.

The generated gases fill the expansion chamber 22 and, when the pressure is sufficient, exert a pressure on the liquid column formed by the two plunger stoppers 32, 34 and the liquid active ingredient 26, the liquid active ingredient 26 is then expelled by the channels 42.

The description of the present disclosure is given as a non-limiting example.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A needleless injection device including:
   a body;
   a gas generator;
   an injection system that extends axially along an injection axis and that comprises, from upstream to downstream along an injection direction, a plunger, a reservoir containing an active ingredient, and an injection nozzle that delimits at least one injection channel;
   a cover that houses the body of the injection device;
   a removable cap adapted to protect a lower downstream end of the injection nozzle;
   a stopper that houses the removable cap and is pivotally mounted about the injection axis between a closed position in which the stopper is locked on the injection device and an open position in which the stopper is unlocked from the injection device; and
   a blocking element that is radially interposed between the removable cap and the stopper, the blocking element being configured to block by friction the relative pivoting of the removable cap and of the stopper, about the injection axis, during pivotal driving of the stopper,
   wherein the stopper includes a tubular portion that delimits a housing adapted to house the removable cap and the lower downstream end of the nozzle, the tubular portion is closed at a downstream end by a removable bottom disc, the removable bottom disc includes a plurality of tightening tabs that extend axially from an upper face of the removable bottom disc and are each designed to bear radially on the blocking element to pinch and block pivotally the blocking element.

2. The needleless injection device according to claim 1, wherein the blocking element is a ring which is fastened on a cylindrical peripheral wall of the removable cap about the injection axis.

3. The needleless injection device according to claim 1, wherein the blocking element is made of an elastically-deformable material.

4. The needleless injection device according to claim 1, wherein the blocking element is made of an elastomer.

5. The needleless injection device according to claim 1, wherein the blocking element is made by overmolding on the removable cap.

6. The needleless injection device according to claim 1, wherein each tightening tab is elastically deformable at least radially toward a center of the removable bottom disc.

7. The needleless injection device according to claim 1, wherein each tightening tab has an axial rib, forming a tooth, that is adapted to penetrate in a substantially radial manner into the blocking element in order to block pivotally the blocking element relative to the stopper.

8. The needleless injection device according to claim 1, wherein each tightening tab bears radially against an inner wall of the stopper to constrain the tightening tabs radially toward the blocking element.

9. The needleless injection device according to claim 1, wherein the removable cap has a generally annular collar that extends about the injection axis and is adapted to cooperate with the lower downstream end of the nozzle.

10. The needleless injection device according to claim 1, wherein the injection device includes a first bayonet-type lock configured to lock the stopper on the body of the injection device, during the driving of the stopper between the open position and the closed position.

11. The needleless injection device according to claim 1, wherein the injection device includes a second bayonet-type lock adapted to lock the removable cap on the nozzle during the driving of the stopper between the open position and the closed position.

12. The needleless injection device according to claim 1, wherein the active ingredient contained in the reservoir is selected from the group consisting of: Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medroxyprogesterone acetate, Medroparin calcium, Methylprednisolone acetate, Heparin calcium, Terbutaline.

* * * * *